United States Patent [19]

Masch

[11] Patent Number: 4,696,667
[45] Date of Patent: Sep. 29, 1987

[54] INTRAVASCULAR CATHETER AND METHOD

[76] Inventor: Helmut Masch, 764 Asbury St., San Jose, Calif. 95126

[21] Appl. No.: 841,879

[22] Filed: Mar. 20, 1986

[51] Int. Cl.⁴ ............................................. A61B 17/20
[52] U.S. Cl. ..................................... 604/22; 128/304; 128/305; 128/752; 604/53
[58] Field of Search ........................ 604/22, 27, 35, 43, 604/52, 53, 164, 165, 266, 267; 128/305, 304, 303 R, 311, 318, 325, 328, 348.1, 751, 752, 755–758, 772; 30/204, 205, 240; 15/104.35 N

[56] References Cited

U.S. PATENT DOCUMENTS

| | | | |
|---|---|---|---|
| 3,565,062 | 2/1971 | Kuris | 128/303 R |
| 3,614,953 | 10/1971 | Moss | 128/305.1 |
| 3,730,185 | 5/1973 | Cook et al. | 128/305 |
| 3,749,085 | 7/1973 | Willson et al. | 128/305 |
| 4,168,708 | 9/1979 | Lepley, Jr. et al. | 128/325 |
| 4,249,541 | 2/1981 | Pratt | 604/165 |
| 4,299,226 | 11/1981 | Banka | 604/53 |
| 4,445,509 | 5/1984 | Auth | 128/305 |
| 4,496,342 | 1/1985 | Banko | 604/27 |
| 4,573,966 | 3/1986 | Weikl et al. | 604/53 |
| 4,589,412 | 5/1986 | Kensey | 128/305.1 |

FOREIGN PATENT DOCUMENTS

| | | | |
|---|---|---|---|
| 2804015 | 8/1979 | Fed. Rep. of Germany | 128/305 |
| 3522649 | 1/1986 | Fed. Rep. of Germany | 128/328 |
| 0764684 | 9/1980 | U.S.S.R. | 128/325 |

Primary Examiner—C. Fred Rosenbaum
Assistant Examiner—Mario Costantino
Attorney, Agent, or Firm—Phillips, Moore, Lempio & Finley

[57] ABSTRACT

An intravascular catheter includes a flexible guide wire mounted for relative rotational and reciprocal movements within a reciprocal and flexible first tube or sheath. A rotary and flexible second tube is mounted for relative reciprocal movement on the first tube and has a rotary inner cutting head secured on an end thereof. The inner cutting head is closely fitted within an outer cutting head that is slidably mounted on the first tube. In carrying out the method of this invention, a blockage in a blood vessel, such as a coronary artery, is located and the outer cutting head engages the blockage to cut the blockage into fragments in response to rotation of the inner cutting head. The fragments are flushed-out from the inner cutting head and are drained through an evacuated annular passage defined between the first and second tubes.

23 Claims, 5 Drawing Figures

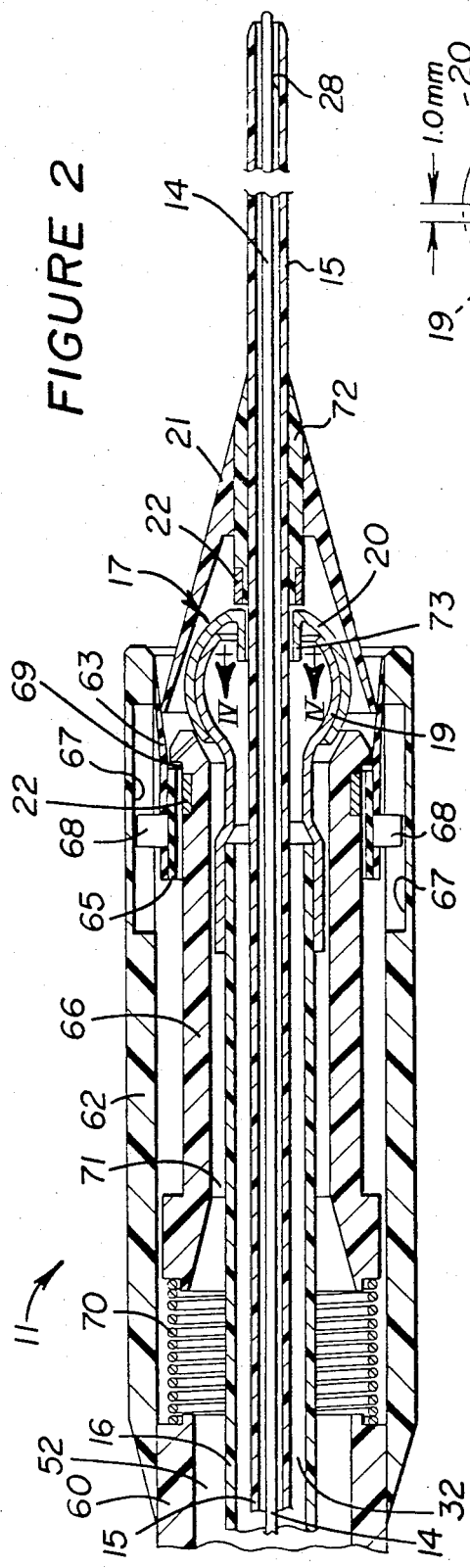
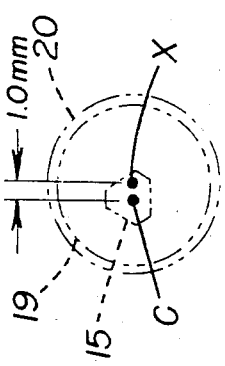
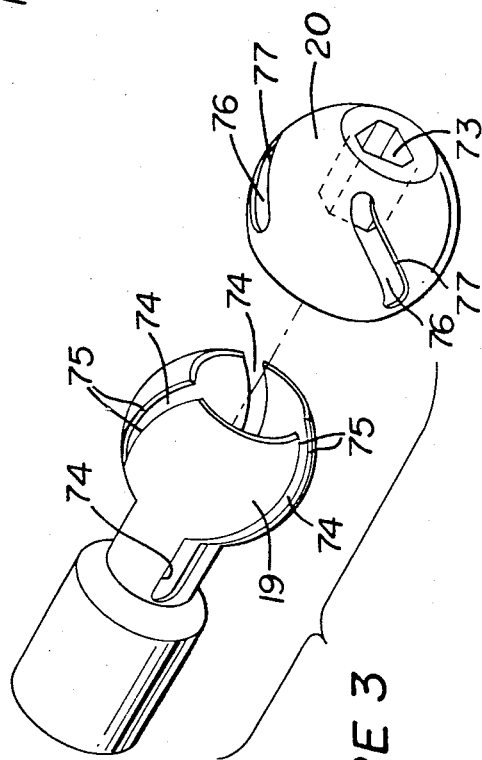
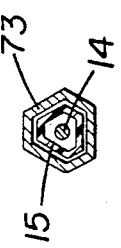

4,696,667

INTRAVASCULAR CATHETER AND METHOD

TECHNICAL FIELD

This invention relates to a medical device for surgically cleaning blood vessels and more particularly to a catheter adapted to be inserted into a blood vessel to cut a blockage therein into particles to restore the vessel to its normal or near normal condition.

BACKGROUND OF THE INVENTION

Coronary arteries carry blood to the muscles of the heart. Any blockage occurring in these arteries, such as by cholesterol build-up, calcific plaque or by clotting, can give rise to serious heart disease. In particular, when the blood supply to a part of the heart is completely cut-off, the affected area of the heart muscle may cease to function.

Medical procedures and therapy for clearing blockages of this type have included the use of chemicals to dissolve the blockage, conventional bypass surgery, laser techniques to fragment and remove the blockage, and mechanical devices to clear or compress the blockage. Such conventional procedures each has obvious limitations and dangers associated with its use.

SUMMARY OF THE INVENTION

An object of this invention is to provide an intravascular catheter and method for clearing blocked blood vessels efficiently, economically and safely.

In its broadest terms, the catheter comprises guide means for locating a blockage in a blood vessel, and rotary cutting means for engaging and cutting the blockage in the vessel into fragments.

In the preferred embodiment, the guide means comprises a flexible guide wire for locating the artery, a flexible first tube having the guide wire mounted for relative rotational and reciprocal movement therein, and the rotary cutting means comprises a rotary flexible second tube having the first tube mounted therein and a cutter secured to the second tube for rotating into engagement with the blockage in response to rotation of the second tube.

The method for clearing the blockage comprises the steps of locating the blockage and engaging the blockage with the rotary cutting means to cut the blockage into fragments. In the preferred method, the fragments are flushed-out from adjacent the cutter and evacuated through the catheter.

BRIEF DESCRIPTION OF THE DRAWINGS

Other objects and advantages of this invention will become apparent from the following description and accompanying drawing wherein:

FIG. 2 is an enlarged view similar to FIG. 1, but illustrates only the catheter in its retracted condition;

FIG. 3 is an enlarged exploded view of inner and outer cutting heads of the catheter;

FIG. 4 is a cross-sectional view, taken in the direction of arrows IV—IV in FIG. 2; and FIG. 5 illustrates an alternate eccentric mounting arrangement for the cutting heads.

BEST MODE OF CARRYING OUT THE INVENTION

General Description

Figure 1:
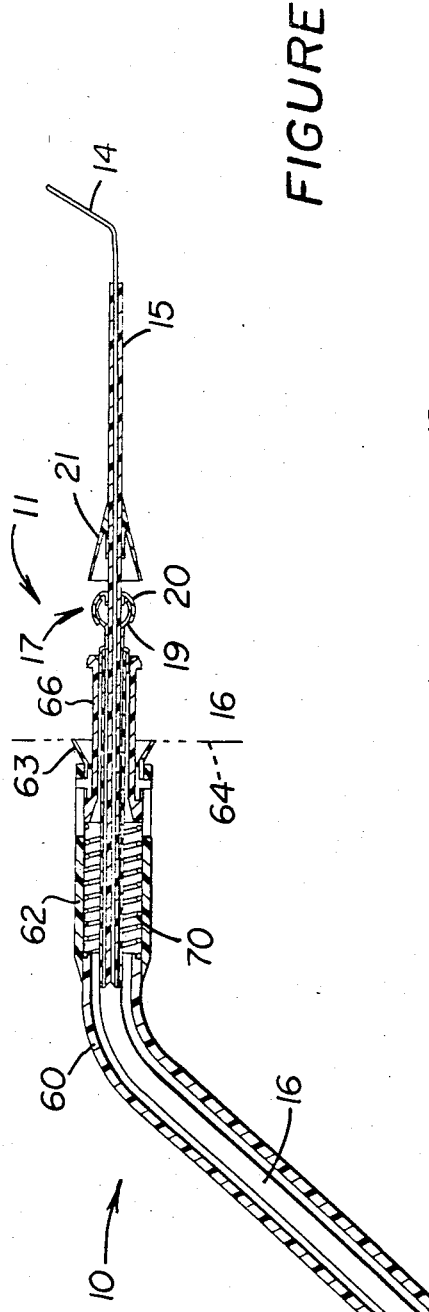
FIG. 1 illustrates a catheter assembly embodying this invention, suitably sectioned to clearly show component parts and showing a catheter of the assembly in its extended condition.
Figure 1:
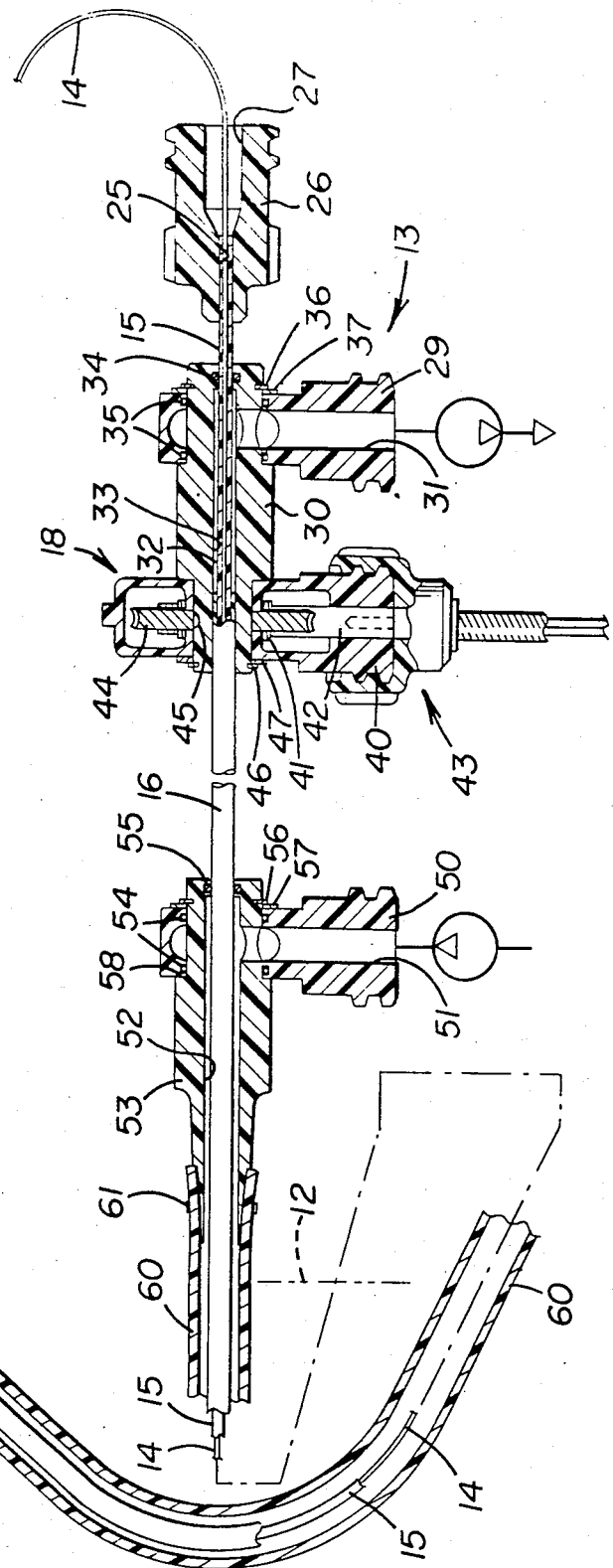

FIG. 1 illustrates a catheter assembly 10, including a catheter 11 adapted to be inserted percutaneously through the skin 12 of a patient and an operator-controlled assembly 13 positioned outside the skin. The illustrated assembly in FIG. 1 has been enlarged approximately five times over an actual assembly for clarification purposes (FIG. 2 is approximately 10:1). The catheter is adapted to be inserted into the femoral artery and abdominal aorta of a patient or into the abdominal aorta directly, through an incision made in the patient in a conventional manner. A flexible guide wire 14 is rotatably and reciprocally mounted in catheter 11 to guide the catheter through the aorta for purposes of locating a coronary artery.

A flexible first tube or sheath 15 has guide wire 14 mounted therein to project from a distal end thereof and is mounted for reciprocal movement in a flexible second tube 16. A cutting means 17 is adapted to engage and cut a blockage in the coronary artery into fragments in response to rotation of second tube 16, driven by a drive assembly 18, described in detail hereinafter. The blockage may be the result of cholesterol build-up, plaque, blood clots or the like.

As shown in FIG. 2 and 3, cutting means 17 comprises a generally spherically shaped inner or male cutting head 19 secured on an end of second tube 16 for simultaneous rotation therewith and a spherically shaped outer or female cutting head 20 mounted for reciprocal movements on first tube 15. As described more fully hereinafter, cutting heads 19 and 20 have overlying blades formed thereon for engaging and cutting the blockage in the artery into fragments in must the same manner that a rotary type razor functions to shave a man's whiskers.

In carrying forth the method, the blockage in the coronary artery of a patient is precisely located and marked using conventional X-ray techniques. Catheter 11 is then inserted into the aorta of the patient with guide wire 14 being utilized to locate the blocked coronary artery and guide the catheter therein. Guide wire can be reciprocated and twisted for this purpose.

A conically shaped strainer cup and seal 21 is secured on tube 15 and spaced bands of a standard magnetic material 22 are suitably formed on the catheter whereby location of the bands relative to the blockage in the coronary artery can be readily detected by conventional X-ray equipment or fluroscopy techniques. Alternatively, visualization of the straining cup or other components of the catheter can be achieved by fluroscopy using the guide wire and/or a radio opaque portion of applicable components of the catheter for detection purposes. The flexible cup is pushed through the blockage and expands automatically to seal-off the downstream side of the coronary artery, relative to the blockage. Simultaneously, the catheter will expand to its extended position, illustrated in FIG. 1. The cup is composed of a material that is sufficiently porous to allow an oxygen-enriched fluid, such as a suitable fluro carbon or blood plasma, to pass through the cup to reach the heart.

Cutting means 17 is then reciprocated on tube 15 to engage the cutting means with the blockage to cut it into fragments. As described more fully hereinafter, the oxygen-enriched fluid that is pumped into cup 21 to supply the heart muscles with their needed nourishment, also functions to flush-out the cut fragments. Although this invention is particularly useful for fragmenting and cleaning-out blockage in coronary arteries, it should be understood that it has other medical and therapeutic applications, such as the cleaning out of veins.

Detailed Description

Referring to FIG. 1, operator-controlled assembly 13 of catheter assembly 10 is maintained exteriorly of the body of the patient. A proximal end of first tube 15 is suitably secured within a bore 25 defined in a housing 26. An inlet passage 27 is defined in the housing in axial alignment with an annular passage 28 (FIG. 2) defined between guide wire 14 and tube 15 to selectively communicate a suitably pressurized medicinal liquid, blood plasma or the like therethrough and/or to monitor the level of blood pressure.

A second housing 29 rotatably mounts a tubular shaft and connector 30 thereon and has a drain passage 31 adapted for connection to a vacuum source. The passage is constantly maintained in fluid communication with an annular passage 32, defined between tube 15 and a bore 33 formed axially through the center of shaft 30 and further defined between tubes 15 and 16 (FIG. 2). A proximal end of passage 32 is closed and sealed by an O-ring 34, mounted between tube 15 and shaft 30, and a pair of axially spaced O-rings 35 are mounted between housing 29 and shaft 30. A snap ring 36 and a washer 37 retain the proximal end of shaft 30 in a fixed axial position, relative to the housing.

Drive assembly 18, adapted to sequentially rotate shaft 30, second tube 16 and thus inner cutting head 19 of cutting means 17, comprises a third housing 40 rotatably mounting a worm gear 41 and a drive shaft 42 for the gear therein. The shaft has a standard drive connection 43 adapted to be coupled to a conventional motorized drive input (not shown) for rotating the shaft and worm gear in a controlled manner. The worm gear meshes with an output 44 that is keyed at 45 to shaft 30. A snap ring 46 and washer 47 retain the distal end of shaft 30 in a fixed position relative to housing 40. As shown, a proximal end of tube 16 is adhesively bonded or otherwise suitably secured within bore 33 whereby the tube will provide a drive input to inner cutting head 19 of cutting means 17.

A fourth housing 50 functions as a rotary joint and fluid connector for supplying the above mentioned oxygen enriched fluid (e.g., blood plasma) to cutting means 17 and strainer cup 21. In particular, an inlet passage 51 is defined in housing 50 to communicate with an annular passage 52, defined between a tubular connector 53 mounted on housing 50 and tube 16. A pair of axially spaced O-ring seals 54 are mounted between housing 50 and connector 53 to seal-off passages 51 and 52 and an O-ring seal 55 is mounted between the connector and tube 16 to seal-off the proximal end of passage 52. The connector is held in a fixed axial position, relative to housing 50, by a snap ring 56 and a washer 57 and an annular shoulder 58 formed on the connector.

A flexible third tube 60 has a proximal end thereof secured on a tapered down end of connector 53 by a ring or band clamp 61. It can thus be understood from the above description that manipulation of housing 26, connector 30 (and attached housings 29, 40), and housing 50 will individually control the movements of tubes 15, 16 and 60, respectively.

Tube 60, as well as tubes 15 and 16, may comprise a standard smooth surface, medium to high density polyethylene or other suitable plastic material used in conventional biomedical devices. The distal end of tube 60 is adhesively bonded in a tubular guide sleeve 62 which thus forms a fixed extension of the tube. As shown in FIG. 2, when the catheter is in its retracted condition of operation for either insertion into or removal from a patient, component parts of the catheter are substantially housed in a protected position within guide sleeve 62. A collapsible frusto-conically shaped entrance seal 63 is reciprocally mounted within a distal end of guide sleeve 62 to seal-off the downstream side (relative to the heart) of the coronary artery from the aorta, as generally depicted at imaginary plane 64 in FIG. 1.

Entrance seal 63 is suitably secured on an annular mounting sleeve 65, reciprocally mounted on a pilot sleeve 66. A pair of longitudinally extending and diametrically opposed guide slots 67 are formed internally on guide sleeve 62 to slidably mount radially extending guide lugs 68, formed integrally on annular mounting sleeve 65, therein. As shown in FIG. 2, when pilot sleeve 66 is retracted within guide sleeve 62 in response to retraction of tube 15, entrance seal will collapse and will be retracted within the guide sleeve by its engagement with an annular shoulder 69 formed on the distal end of pilot sleeve 66. The entrance seal is composed of a thin walled silicone or other highly flexible plastic material approved for medical uses of this type that will permit the frusto-conically shaped seal to collapse and fold radially inwardly to facilitate such retraction.

A compression coil spring 70 is mounted within guide sleeve 62, axially between tube 60 and an end of sleeve 66, to bias pilot sleeve 66 rightwardly to its extended position, illustrated in FIG. 1. Passage 52, defined between tubes 16 and 60, communicates with an annular passage 71 defined between tube 16 and pilot sleeve 66 to communicate the above-mentioned oxygen enriched fluid over cutting means 17 to supply the fluid to the heart and to flush-out the fragments of the blockage severed by the cutting means. A vacuum is drawn at drain passage 31, defined in housing 29, so that the fragment-laden fluid is drained through the catheter via passage 32, defined between tubes 15 and 16.

As shown in FIG. 4, the outer surface of tube 15 is formed with a triangular configuration from approximately the point whereat the tube enters guide sleeve 62 to the distal end thereof whereat guide wire 14 projects forwardly therefrom. A mounting sleeve 72, having straining cup 21 suitably secured thereon, has an internal triangular configuration conforming to the outer configuration of tube 15. The mounting sleeve is adhesively bonded to tube 15 whereby the strainer cup will reciprocate with the tube. Outer cutting head 20 is slidably mounted on tube 15 by an integral mounting sleeve 73 that is internally configured triangularly (FIG. 4) to match the outer configuration of tube 15 whereby the outer cutting head can reciprocate on the tube, but cannot rotate relative thereto.

As shown in FIG. 3, inner cutter head 19 is mounted in protected relationship within outer cutting head 20 and has a plurality of diagonal slots 74 formed therethrough to define a plurality of circumferentially spaced cutting blades 75 on cantilevered elements thereof. Likewise, outer cutting head 20 has a plurality of diagonal slots 76 formed therethrough to define a plurality of circumferentially spaced cutting blades 77. Blades 75 and 77 cross-over each other during the cutting action and each blade is preferably disposed at an acute angle relative to a longitudinal and rotational axis x of cutting means 17 and tube with the blades being disposed to define an included acute angle therebetween, preferably selected from the approximate range of from 10° to 20°. The cantilevered elements of the inner cutting head are sufficiently resilient and flexible to permit the outer cutting head to "snap-on" the inner cutting head when they are assembled together.

Straining cup 21 is preferably composed of a porous plastic material having a porosity in the range of 50 microns, for example. A typical plastic material for this purpose may constitute the Interflo ® porous plastic material manufactured by Chromex Corp. of Brooklyn, N.Y. which has a porosity controllable within the range of from 10 to 150 microns and exhibits 10%–60% in void volume whereby flow control and filtration can be accurately maintained. Likewise, mounting sleeve 72 and the portion of tube 15 extending on the downstream side of cutting means 17 (towards strainer cup 21) can be formed of a porous plastic material of this type to continuously ensure the desired amount of oxygen to the heart.

Guide wire 14 may constitute a standard Teflon (polytelrafluroethylene) coated steel wire having a diameter in the approximate range of from 0.89 mm to 0.97 mm. The distal portion of the wire, approximately from cutting means 17 (FIG. 1) to the distal end of the wire, can be finely coiled in a conventional manner. The remaining portion of the wire is fabricated to be normally straight and uncoiled.

As schematically shown in FIG. 5, the center C of outer cutting head 20 can be mounted eccentrically on tube 15 and relative to longitudinal and normal rotational axis x of tube 15. For example, for an outer cutting head having an outside diameter of 3.0 mm and an eccentricity of 1.0 mm, the effective cutting diameter of cutting means 17 becomes 5.0 mm. Thus, the cutting head can be inserted into an artery to favor one side thereof and effectively cut-out blockages on the other side of the artery. Inner cutting head 19 will, of course, follow the position of the outer cutting head due to the inherent flexibility of tube 16. It should be understood that the outer diameter of the cutting means, whether concentric or eccentric, will depend on the surgical procedure and sizes of the blood vessels and blockages under consideration.

Method of Operation

Catheter 11 is inserted percutaneously into the aorta of a patient in its retracted condition illustrated in FIG. 2. The distal end of tube 15 can be frusto-conically shaped to facilitate such insertion. Prior to insertion of the catheter through skin 12 of the patient, an oxygen-enriched fluid, such as a suitably composed blood plasma or an oxygen enriched flurocarbon, is pumped within a normal blood pressure range from inlet 51 (FIG. 1) through passasges 52, 71, slots 14 and passage 32 to evacuate any air in the catheter back to outlet or drain 31.

Guide wire 14 is used as a probe to guide the catheter to the blockage in the coronary artery of the patient with conventional x-ray or fluroscopy techniques being utilized to detect bands of magnetic material 22. When the artery is located, tubes 15 and 16 are suitably reciprocated to permit spring 70 to expand the catheter to its FIG. 1 extended position and to properly position strainer cup 21 and entrance seal 63 at the upstream and downstream sides of the blockage, respectively. The straining cup 21, now positioned to seal-off the downstream side of the coronary artery, is constructed of a sufficiently thin and flexible plastic material to enable it to expand-out to its FIG. 1 sealing condition against the inner wall of the coronary artery.

Once straining cup 21 and entrance seal 63 are precisely positioned in the coronary artery upon manipulation and reciprocation of tubes 15, 16 and 60, the operative procedure can commence. The entrance seal now seals-off the upstream side of the coronary artery from the aorta and, along with strainer cup and seal 21, will prevent fragments of the thereinafter cut-up blockage from regressing into the patients aorta or progressing into the heart proper.

Housings 29 and 40 and thus tube 16 are then moved in a controlled manner to extend cutting means 17, relative to pilot sleeve 66, into gradual cutting engagement with the blockage. It is contemplated that shaft 42 of drive assembly 18 will be rotated at speeds in the approximate range of from 10 rpm to 60 rpm under control of the operator to efficiently cut the blockage into fragments. Simultaneously therewith, the oxygen-enriched fluid, is being continuously communicated under a normal blood pressure range to inlet passage 51 of housing 50 and thence through passages 52 and 71 to the cutting means.

The fluid will pass through slots 74 and 76 of the cutting means to flush-out the fragments and return the fragment-laden fluid back through drain passage 31, via passage 32 defined between tubes 15 and 16, under influence of the partial vacuum drawn at passage 31. Any residue fragments will be captured and retained within cup 21 and the catheter proper, upon retraction of tube 15 and the catheter to its FIG. 2 condition and removal of the catheter from the patient's body. The cut fragments collect naturally within the inner cutting head 19 and are retained therein with the aid of the pressurized fluid.

As described above, the oxygen-enriched fluid communicated to the coronary artery from inlet passage 51 will have a portion thereof pass through the straining cup to supply the coronary artery and heart with sufficient oxygen at an appropriate pressure to maintain it in a healthy condition. Passage 51, as well as passage 27 defined in housing 26, can be used to inject any necessary type of medicinal fluid to the coronary artery, if so desired. Also, passage 27 and its communicating passage 28 can also be utilized to monitor the blood pressure of the patient. Passages 28 and 32 are clearly shown in FIG. 2, but are obscure in FIG. 1 due to the reduced scale of this drawings Figure.

I claim:
1. An intravascular catheter for clearing a blockage in a blood vessel or the like comprising
   flexible guide means for locating said vessel,
   a flexble first tube having said guide means mounted for relative rotational and reciprocal movement therein,
   a rotary flexible second tube having said first tube mounted for relative reciprocal movement therein,
   means for selectively rotating said second tube, and
   cutting means for cutting said blockage into fragments in response to rotation of said second tube comprising an outer cutting head mounted on said first tube, an inner cutting head rotatably mounted in protected relationship within said outer cutting head and connected to said second tube for simultaneous rotation therewith and cooperating blade means between said outer and inner cutting heads for cutting said blockage.

2. The catheter of claim 1 wherein said guide means comprises an elongated and flexible wire.

3. The catheter of claim 2 further comprising an annular passage defined between said wire and said first tube, said passage extending throughout the length of said first tube from a proximal to a distal end thereof.

4. The catheter of claim 1 further comprising first sealing means secured on said first tube between a distal end thereof and distally of said cutting means for sealing said vessel.

5. The catheter of claim 4 wherein said first sealing means comprises a frusto-conically shaped straining cup composed of a flexible plastic material have a porosity sufficient to permit the passage of a fluid therethrough.

6. The catheter of claim 4 further comprising a flexible third tube having said first and second tubes mounted therein and second sealing means mounted on a distal end of said third tube and proximally of said cutting means for sealing said vessel.

7. The catheter of claim 6 further comprising an outer guide sleeve secured on a distal end of said third tube to form an extension thereof and means for reciprocally mounting said second sealing means on the distal end of said guide sleeve.

8. The catheter of claim 7 wherein said second sealing means comprises a frusto-concially shaped entrance seal diverging towards said cutting means, said entrance seal composed of a flexible plastic material adapted to collapse and fold radially inwardly into said guide sleeve.

9. The catheter of claim 8 further comprising a pilot sleeve reciprocally mounted in said outer guide sleeve and wherein said entrance seal is reciprocally mounted on said pilot sleeve.

10. The catheter of claim 8 further comprising compression coil spring means mounted between said third tube and said pilot sleeve for biasing said pilot sleeve away from said third tube.

11. The catheter of claim 9 further comprising an annular passage defined between said second and third tubes communicating with an annular passage defined between said second tube and said pilot sleeve and terminating at an outlet at a distal end thereof adjacent to said cutting means.

12. The catheter of claim 6 wherein said cutting means is positioned axially between said first and second sealing means when said catheter is extended to separate said first and second sealing means from each other, said outer cutting head slidably mounted on said first tube and said inner cutting head secured on a distal end of said second tube.

13. The catheter of claim 1 wherein each of said inner and outer cutting heads are at least generally spherically shaped and said blade means comprises a plurality of circumferentially spaced cutting blades formed on said inner and outer cutting heads.

14. In an intravascular catheter for clearing a blockage in a blood vessel or the like, the invention comprising
a rotatable elongated flexible tubular drive member,
an elongated tubular catheter mounted within the drive member,
guide means for locating said vessel, and
rotary cutting means for engaging and cutting said blockage into fragments comprising, an inner cutting head attached to said drive member to rotate simultaneously therewith and rotatably mounted in protected relationship within an outer cutting head, said outer cutting head attached to the catheter, and cooperating blade means between said inner and outer cutting heads for cutting said blockage into fragments.

15. The catheter of claim 14 further comprising flushing means for flushing-out said fragments from adjacent said rotary cutting means.

16. The catheter of claim 15 further comprising first sealing means mounted on said catheter distally of said rotary cutting means for sealing an upstream side of said blood vessel and second sealing means mounted proximally of said cutting means for sealing a downstream side of said blood vessel.

17. The catheter of claim 16 wherein each of said first and second sealing means is cup-shaped and face each other in diverging relationship towards said cutting means.

18. The catheter of claim 15 wherein said flushing means comprises passage means defined through said catheter and terminating at an outlet adjacent to said rotary cutting means for communicating a pressurized fluid to said cutting means, means defining openings through said cutting means for receiving said fluid and passing said fluid through said cutting means and internally thereof and outlet passage means defined in said catheter for receiving fragment-laden fluid from internally of said cutting means and draining said fluid from said catheter.

19. The device of claim 14 wherein said blade means comprise a plurality of circumferentially spaced cutting blades formed on said inner and outer cutting heads.

20. A method for clearing a blockage in a blood vessel comprising the steps of
locating said vessel and blockage, and
subjecting said blockage to a rotary cutting action by a rotary cutter to cut said blockage into fragments, including the steps of engaging said blockage with a relatively non-rotating outer cutting head of said rotary cutter and rotating inner cutting head of said rotary cutter rotatably mounted within said outer cutting head.

21. A method of claim 20 further comprising flushing-out said fragments.

22. The method of claim 21 further comprising sealing-off said blood vessel at upstream and downstream sides of said blockage, distally and proximally of said rotary cutter, respectively.

23. The method of claim 22 further comprising permitting controlled fluid flow to pass through the sealed upstream side of said blockage and into said blood vessel.

* * * * *